(12) United States Patent
Wang et al.

(10) Patent No.: US 7,195,746 B2
(45) Date of Patent: *Mar. 27, 2007

(54) INTERIOR SURFACE MODIFICATIONS OF MOLECULAR SIEVES WITH ORGANOMETALLIC REAGENTS AND THE USE THEREOF FOR THE CONVERSION OF OXYGENATES TO OLEFINS

(75) Inventors: Kun Wang, Bridgewater, NJ (US); Richard Earl Bare, North Brunswick, NJ (US); Doron Levin, Annadale, NJ (US); James Clark Vartuli, Schwenksville, PA (US); Guang Cao, Branchburg, NJ (US); Richard B. Hall, Whitehouse Station, NJ (US)

(73) Assignee: Exxon Mobil Chemical Patents Inc., Houston, TX (US)

( * ) Notice: Subject to any disclaimer, the term of this patent is extended or adjusted under 35 U.S.C. 154(b) by 97 days.

This patent is subject to a terminal disclaimer.

(21) Appl. No.: 10/377,192

(22) Filed: Feb. 28, 2003

(65) Prior Publication Data

US 2003/0187314 A1    Oct. 2, 2003

Related U.S. Application Data

(63) Continuation of application No. 10/112,250, filed on Mar. 29, 2002, now Pat. No. 6,759,360.

(51) Int. Cl.
*C01B 37/04* (2006.01)
*C01B 37/08* (2006.01)

(52) U.S. Cl. ............... 423/305; 423/306; 423/DIG. 30; 502/85; 502/208; 502/214

(58) Field of Classification Search ............... 423/713, 423/714, 715, 305, 306, 326, DIG. 30; 502/85, 502/208, 214
See application file for complete search history.

(56) References Cited

U.S. PATENT DOCUMENTS 3,258,455 A    6/1966    Natta et al. ................. 260/93.7

(Continued)

FOREIGN PATENT DOCUMENTS

EP    B 77523    5/1985

(Continued)

OTHER PUBLICATIONS

Kostapapas, A., "*Preparation and Characterization of Iron Catalysts on Pillared Clays and Phosphorus—Containing Molecular Sieves*", Abstract, retrieved from STN Database accession No. 88:7463 XP002256217, Univ. of Conn., Diss. (1987).

(Continued)

Primary Examiner—David Sample

(57) ABSTRACT

A method for making an organometallic treated molecular sieve is described in which a molecular sieve having at least one hydroxyl group and at least [AlO$_2$] and [PO$_2$] tetrahedral units and having an average pore dimension less than or equal to about 5 Å is contacted with a solution comprising an organometallic compound and a non-proton donating solvent. The resulting organometallic treated molecular sieve has enhanced ethylene and/or propylene selectivity when used in the conversion of organic oxygenates to olefins. The ethylene and/or propylene selectivity, as well as catalyst life, are further enhanced when the resulting organometallic treated molecular sieve is combined with an oxide of at least one metal selected from Groups 2, 3 and Group 4 of the Periodic Table.

47 Claims, 4 Drawing Sheets

MAS $^1$H NMR of modified SAPO-34 via different methods

U.S. PATENT DOCUMENTS

| Patent | Type | Date | Inventor | Class |
|---|---|---|---|---|
| 3,305,538 | A | 2/1967 | Natta et al. | 260/93.7 |
| 3,364,190 | A | 1/1968 | Emrick | 260/93.7 |
| 3,645,992 | A | 2/1972 | Elston | 260/80.78 |
| 3,691,101 | A | 9/1972 | Mertzweiller et al. | 252/455 |
| 4,068,136 | A | 1/1978 | Minami | 307/353 |
| 4,076,698 | A | 2/1978 | Anderson et al. | 526/348.6 |
| 4,243,691 | A | 1/1981 | Mohlenkamp, Jr. et al. | 426/649 |
| 4,302,565 | A | 11/1981 | Goeke et al. | 526/88 |
| 4,310,440 | A | 1/1982 | Wilson et al. | 252/435 |
| 4,376,722 | A | 3/1983 | Chester et al. | 252/430 |
| 4,440,871 | A | 4/1984 | Lok et al. | 502/214 |
| 4,444,898 | A * | 4/1984 | Schwartz et al. | 502/62 |
| 4,446,243 | A * | 5/1984 | Chester et al. | 502/62 |
| 4,451,572 | A * | 5/1984 | Cody | 502/62 |
| 4,465,889 | A | 8/1984 | Anthony et al. | 585/640 |
| 4,471,150 | A | 9/1984 | Wu | 585/640 |
| 4,481,376 | A | 11/1984 | Wunder et al. | 585/640 |
| 4,482,752 | A * | 11/1984 | Mitchell et al. | 585/670 |
| 4,499,327 | A | 2/1985 | Kaiser | 585/640 |
| 4,532,225 | A * | 7/1985 | Tsao et al. | 502/62 |
| 4,567,029 | A | 1/1986 | Wilson et al. | 423/306 |
| 4,636,482 | A | 1/1987 | Okado et al. | |
| 4,659,685 | A | 4/1987 | Coleman, III et al. | 502/113 |
| 4,663,305 | A | 5/1987 | Mauldin et al. | 502/304 |
| 4,677,242 | A | 6/1987 | Kaiser | |
| 4,677,243 | A | 6/1987 | Kaiser | |
| 4,692,424 | A | 9/1987 | Le Van Mao | 502/68 |
| 4,861,743 | A | 8/1989 | Flank et al. | 502/214 |
| 4,873,390 | A | 10/1989 | Lewis et al. | |
| 5,070,052 | A | 12/1991 | Brownscombe et al. | 502/60 |
| 5,095,163 | A | 3/1992 | Barger | |
| 5,096,684 | A | 3/1992 | Guth et al. | 423/306 |
| 5,126,308 | A | 6/1992 | Barger et al. | 502/214 |
| 5,294,578 | A | 3/1994 | Ho et al. | 502/62 |
| 5,302,362 | A | 4/1994 | Bedard | 423/306 |
| 5,382,696 | A * | 1/1995 | Kiyoura et al. | 564/479 |
| 5,523,506 | A | 6/1996 | Benazzi et al. | 585/481 |
| 5,559,275 | A | 9/1996 | Barger | 568/905 |
| 5,625,104 | A | 4/1997 | Beck et al. | 585/475 |
| 5,714,662 | A | 2/1998 | Vora et al. | |
| 5,849,968 | A | 12/1998 | Beck et al. | 585/481 |
| 5,892,079 | A | 4/1999 | Wilson, Jr. | 556/11 |
| 5,912,393 | A | 6/1999 | Barger et al. | 585/640 |
| 5,962,762 | A | 10/1999 | Sun et al. | 585/640 |
| 5,981,417 | A | 11/1999 | Drake | 502/64 |
| 6,046,373 | A * | 4/2000 | Sun | 585/640 |
| 6,084,142 | A | 7/2000 | Yao et al. | 585/407 |
| 6,107,534 | A | 8/2000 | Drake et al. | 585/411 |
| 6,166,282 | A | 12/2000 | Miller | |
| 6,180,828 | B1 * | 1/2001 | Hidaka et al. | 564/479 |
| 6,228,799 | B1 | 5/2001 | Aubert et al. | 502/304 |
| 6,743,747 | B1 | 6/2004 | Xu et al. | |
| 6,759,360 | B2 * | 7/2004 | Wang et al. | 502/85 |
| 6,844,291 | B2 | 1/2005 | Levin et al. | |
| 6,864,200 | B2 | 3/2005 | Das et al. | |
| 2001/0002383 | A1 | 5/2001 | Hidaka et al. | 502/72 |
| 2002/0151758 | A1 * | 10/2002 | Das et al. | 585/467 |

FOREIGN PATENT DOCUMENTS

| | | |
|---|---|---|
| EP | A 312981 | 4/1989 |
| EP | B 697247 | 2/1996 |
| EP | A 993867 | 4/2000 |
| GB | 1108262 | 3/1968 |
| WO | WO 97/21652 | 6/1997 |
| WO | WO 97/26989 | 7/1997 |
| WO | WO 02/05952 | 9/1998 |
| WO | WO 00/69796 | 11/2000 |
| WO | WO 01/60746 | 8/2001 |
| WO | WO 98/29370 | 1/2002 |

OTHER PUBLICATIONS

Kang et al., "Effects of decrease in number of acid sites located on the external surface of Ni-SAPO-34 crystalline catalyst by the mechanochemical method", *Catalysis Letters* 53, pp. 171-176 (1998).

Inui, J. Chemical Society Chem. Commun., p. 205, 1990.

* cited by examiner

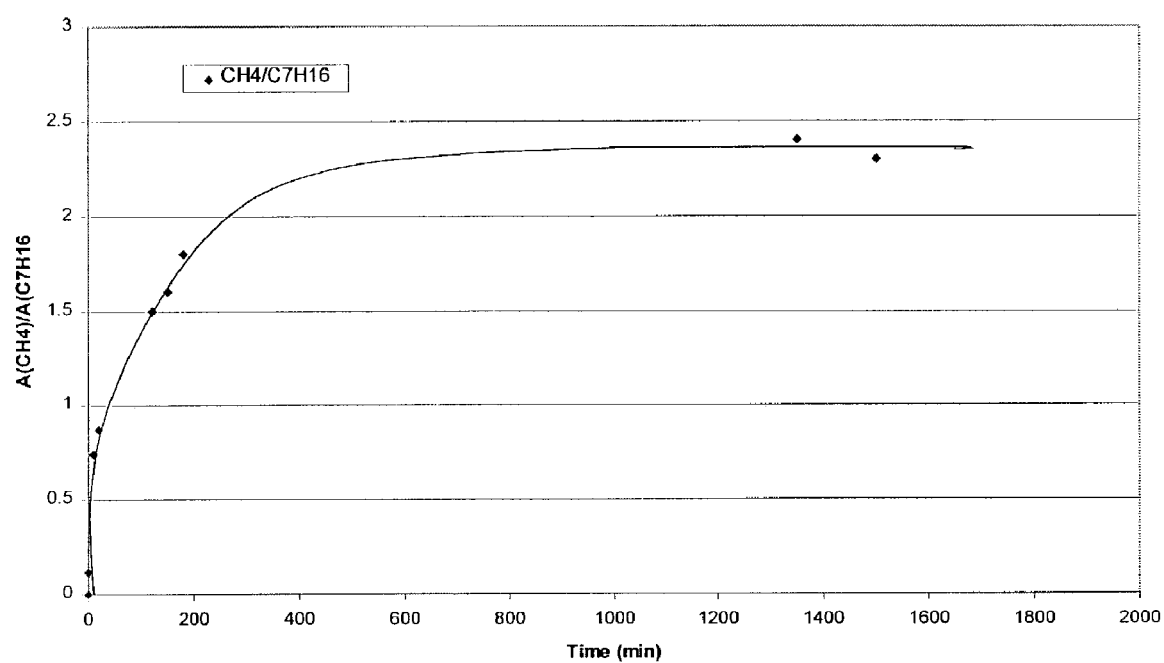
Figure 1. Evolution of methane during ZnMe$_2$ treatment of SAPO-34 in heptane (Example 17)

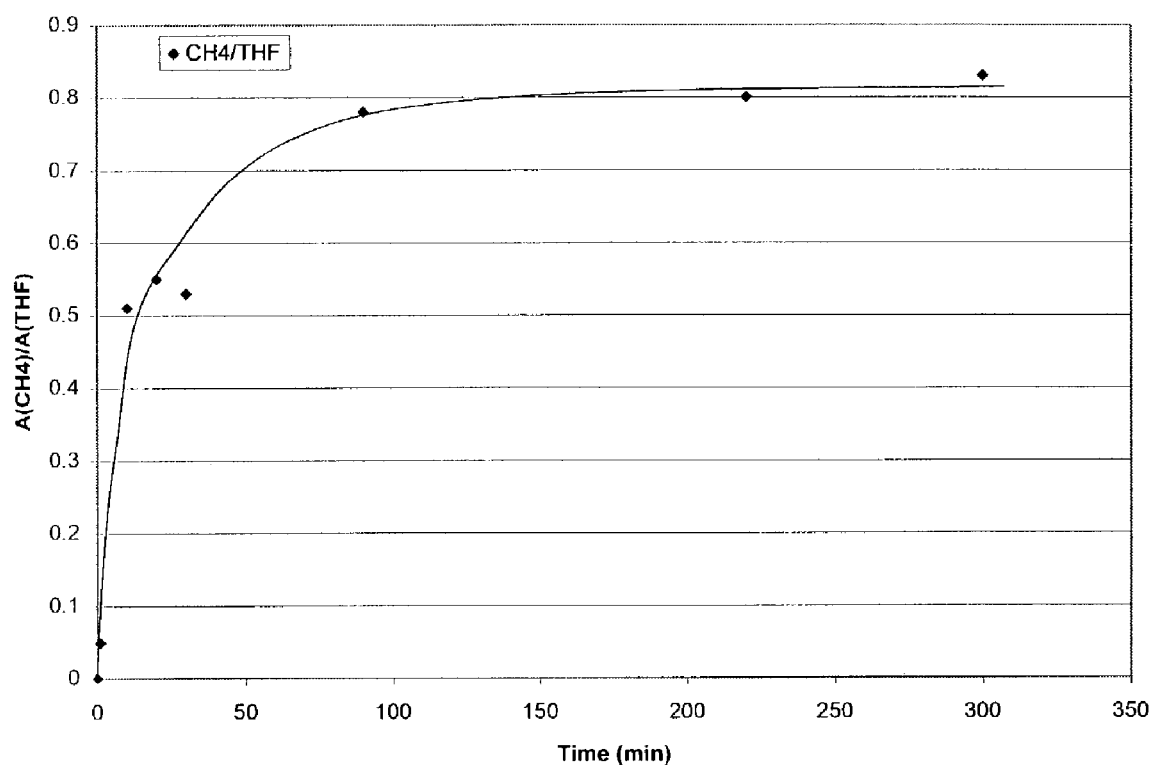
Figure 2. Evolution of methane during MeMgBr treatment of SAPO-34 in toluene/THF (Example 18)

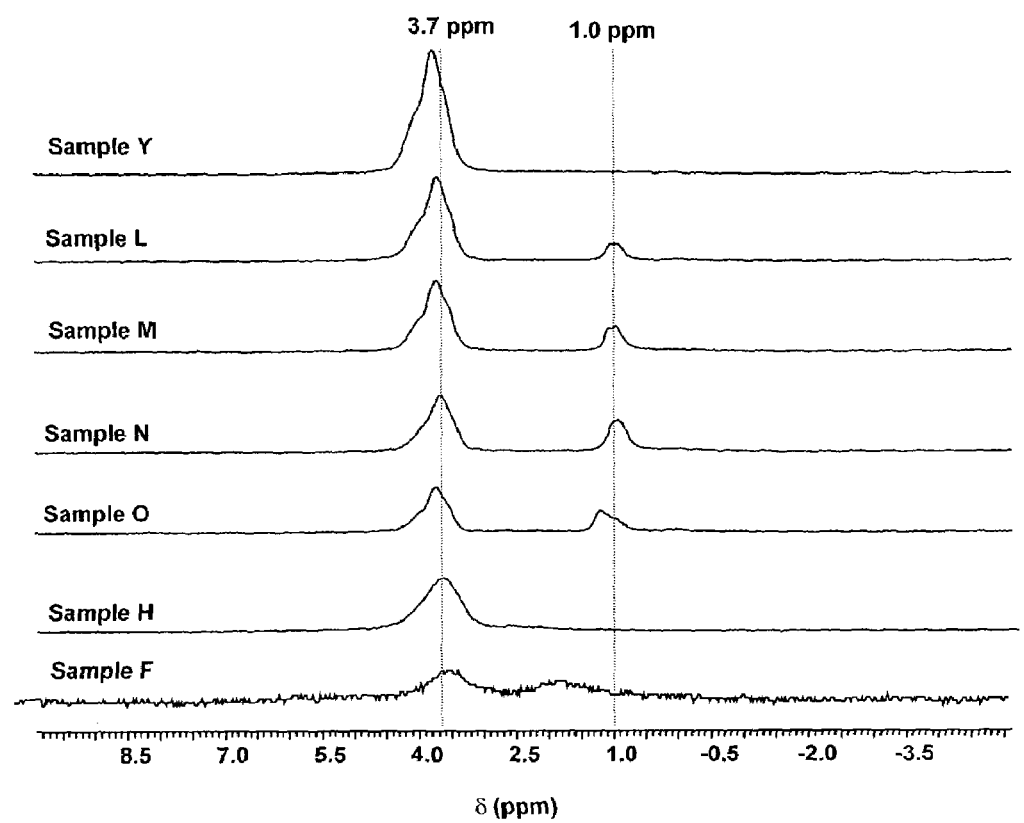
Figure 3. MAS $^1$H NMR of modified SAPO-34 via different methods

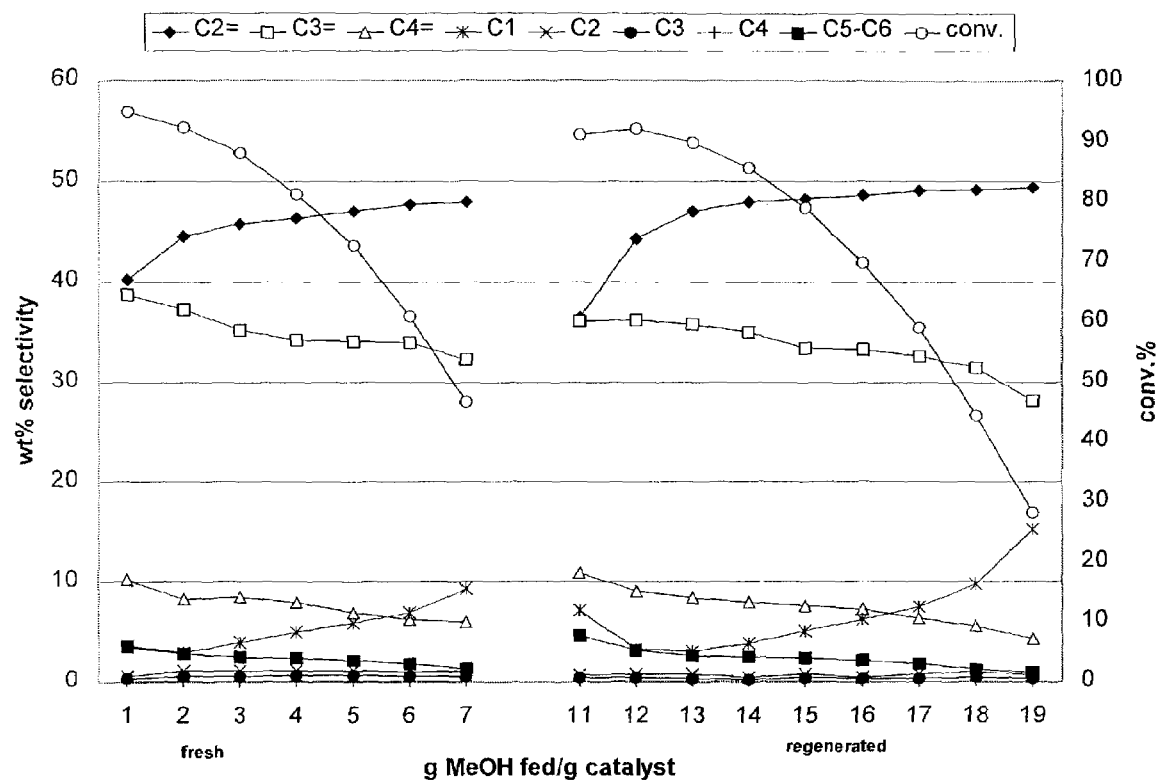
Figure 4. Conversion and selectivity for fresh (left) and regenerated (right) SAPO-34 modified with $ZnMe_2$ (Example 24, Sample B)

INTERIOR SURFACE MODIFICATIONS OF MOLECULAR SIEVES WITH ORGANOMETALLIC REAGENTS AND THE USE THEREOF FOR THE CONVERSION OF OXYGENATES TO OLEFINS

CROSS REFERENCE TO RELATED APPLICATIONS

The present application is a continuing application from U.S. patent application Ser. No. 10/112,250 filed Mar. 29, 2002 now U.S. Pat. No. 6,759,360, the entire contents of which application are incorporated herein by reference.

FIELD

The invention is directed to a method for modifying the interior surface of molecular sieves, particularly aluminophosphate and silicoaluminophosphate molecular sieves, the modified molecular sieves and the use thereof in a method for converting an oxygenate feedstock to a product, including an olefin.

BACKGROUND

Olefins, particularly light olefins, have been traditionally produced from petroleum feedstocks by either catalytic or steam cracking. Oxygenates, however, are becoming an alternative feedstock for making light olefins, particularly ethylene and propylene. Promising oxygenate feedstocks are alcohols, such as methanol and ethanol, dimethyl ether, methyl ethyl ether, diethyl ether, dimethyl carbonate, and methyl formate. Many of these oxygenates can be produced from a variety of sources including synthesis gas derived from natural gas; petroleum liquids; and carbonaceous materials, including coal. Because of the relatively low-cost of these sources, alcohol, alcohol derivatives, and other oxygenates have promise as an economical, non-petroleum source for light olefin production.

One way of producing olefins is by the catalytic conversion of methanol using a silicoaluminophosphate (SAPO) molecular sieve catalyst. For example, U.S. Pat. No. 4,499,327 to Kaiser, discloses making olefins from methanol using a variety of SAPO molecular sieve catalysts. The process can be carried out at a temperature between 300° C. and 500° C., a pressure between 0.1 atmosphere to 100 atmospheres, and a weight hourly space velocity (WHSV) of between 0.1 and 40 $hr^{-1}$.

Inui (*J. Chemical Society Chem. Commun.* p. 205, 1990) has shown that the selectivity to ethylene can be increased when methanol is contacted with a nickel-substituted SAPO-34 rather than an unsubstituted SAPO-34. In this case, nickel substitution occurred into the SAPO-34 framework.

In contrast to the work of Kaiser and Inui, metal incorporation may also take place post-synthesis, that is, following the synthesis of the molecular sieve framework. For example, U.S. Pat. No. 5,962,762 to Sun et al. teaches a process for converting methanol to light olefins using a metal-incorporated SAPO catalyst. The catalyst is produced by allowing a SAPO molecular sieve to remain in contact at ambient conditions with an aqueous metal solution, preferably a nickel or cobalt containing solution, whereby the metal is adsorbed onto the sieve. The treated molecular sieve is then separated from the solution and dried. U.S. Pat. Nos. 5,625,104 and 5,849,968 to Beck at al. teach a process of incorporating alkali and alkaline earth metals into a zeolitic catalyst by pretreating the zeolite with an organosilicon or poly-oxo silicon compound followed by the treatment with a metal solution. U.S. Pat. No. 4,692,424 to Le Van Mao teaches a process for the dry incorporation of manganese ions on the external reactive sites of zinc-containing ZSM-5 and ZSM-11 by adding a minimum amount of an aqueous manganese solution to form a malleable paste and extruding the paste under pressure.

Post-synthesis metal incorporation of zeolite catalysts is also used for other processes. For example, U.S. Pat. No. 6,084,142 to Yao et al. teaches treating a ZSM-5 catalyst with a solution of a zinc component, such as dimethylzinc, followed by steam treatment for the conversion of hydrocarbons to aromatics and lower olefins. There is no teaching of conversion of methanol to olefins.

Yamamoto et al. (*Microporous and Mesoporous Materials* 44–45, Organic Functionalization of Mesoporous Molecular Sieves with Grignard Reagents, p. 459–464, 2001) teach post-synthesis organic functionalization of MCM-41 in a two step procedure. MCM-41 is first modified by alcohols, which leads to the esterification of surface silanol groups (converting Si—OH to Si—OR) and then allowed to react with a Grignard reagent R'MgX which converts Si—OR to Si—R'. Again, there is no teaching of conversion of methanol to olefins.

PCT Application WO 97/26989 teaches a process for producing a catalyst by combining a medium pore, non-zeolitic molecular sieve, such as SAPO-11, SAPO-31 and SAPO-41, with an active source of a hydrogenation component in a non-aqueous solvent. The resultant catalyst is disclosed as being useful for hydrocracking and catalytic dewaxing. There is no teaching of conversion of methanol to olefins.

Although much research has already been undertaken to optimize aluminophosphate and silicoaluminophosphate molecular sieve catalysts for use in the conversion of methanol to light olefins, there remains a need to develop catalysts which show improved selectivity to the desired olefins, ethylene and propylene, and in some cases improved selectivity to ethylene alone. Moreover, since methanol conversion catalysts tend to undergo rapid catalyst deactivation due to the formation of coke, thereby requiring frequent regeneration, there is also a need for catalysts which deactivate more slowly, that is have a longer effective lifetime.

SUMMARY

In one aspect, the present invention resides in a method for making an organometallic treated molecular sieve comprising:

a) providing a molecular sieve having at least $[AlO_4]$ and $[PO_4]$ tetrahedral units, and most preferably $[SiO_4]$, $[AlO_4]$ and $[PO_4]$ tetrahedral units, and having an average pore dimension less than or equal to about 5 Å, such as in the range of from about 3 Å to about 5 Å, the molecular sieve having at least one hydroxyl group;

b) contacting said molecular sieve with a solution comprising an organometallic compound and a non-proton donating solvent, wherein said organometallic compound comprises at least one metal bound to at least one alkyl group; and c) separating the organometallic treated molecular sieve from the solution.

In one embodiment, the method also comprises physically mixing the organometallic treated molecular sieve with at least one metal oxide selected from Group 2, Group 3 and Group 4 of the Periodic Table of Elements.

In a further aspect, the invention relates to an organometallic treated molecular sieve, particularly a silicoaluminophosphate molecular sieve, obtainable by the method of the present invention. The organometallic compound is incorporated into, onto, or within the molecular sieve by chemical reactions to modify both the internal and external surfaces, preferably the internal surface, of the molecular sieve.

The invention further resides in a catalyst comprising an organometallic treated molecular sieve, particularly a silicoaluminophosphate molecular sieve, according to said further aspect the invention.

In yet a further aspect, the invention resides in a process of making an olefinic product, wherein a catalyst comprising an organometallic treated molecular sieve, particularly a silicoaluminophosphate molecular sieve, is contacted with a feedstock comprising at least one organic compound that contains at least one oxygen atom (oxygenate) under conditions suitable to convert the oxygenate into olefins.

Conveniently, the organometallic compound comprises at least one metal bound to at least one alkyl group, such as methyl lithium, butyl lithium, dimethyl zinc, diethyl zinc, ethylmagnesium bromide, methylmagnesium bromide, trimethyl gallium, triethyl gallium, tetraethyl germanium, and tetramethyl germanium.

BRIEF DESCRIPTION OF THE DRAWINGS

FIG. 1 shows the evolution of methane during dimethyl zinc treatment of SAPO-34 in heptane.

FIG. 2 shows the evolution of methane during methylmagnesium bromide treatment of SAPO-34 in a mixture of toluene and tetrahydrofuran (THF).

FIG. 3 shows MAS $^1$H NMR of zinc modified SAPO-34 via different zinc modification methods.

FIG. 4 shows conversion and selectivity data for fresh and regenerated SAPO-34 modified with dimethyl zinc.

DETAILED DESCRIPTION OF THE EMBODIMENTS

This invention relates to treatment of molecular sieves, particularly small pore aluminophosphate and silicoaluminophosphate molecular sieves, with organometallic reagents after the molecular sieve structures have been formed. Post synthesis metal incorporation offers several advantages over that of metal incorporation during molecular sieve synthesis. The physical characteristics of the molecular sieve, such as particle and pore dimensions, can be varied prior to metal incorporation. As a result, post-synthesis techniques provide wider possibilities in molecular sieve preparation and screening.

Post-synthesis modification according to the invention uses organometallic compounds as the modifying reagents. With this modification, metal species are incorporated into or onto the molecular sieve through chemical reaction with hydroxyl groups in the molecular sieve. The proper size of the reagent and the nature of the chemical reactions determine the location, preferably on the interior surface of the molecular sieve, of the metal introduced. Compared to conventional post-synthesis methods, the method of the present invention uses mild conditions and offers control of reaction mechanisms such as the loading of the metal, the site and degree of reaction, and the location of the metal, therefore offering a controllable approach to improve catalyst performance.

When the resultant organometallic modified molecular sieves are used in the catalytic conversion of feedstocks, such as methanol, to light olefins, they exhibit higher selectivities to ethylene and/or propylene than the corresponding unmodified molecular sieve. Moreover, it has been found that combining the organometallic modified molecular sieve with one or more active metal oxides, particularly from Groups 2 to 4 of the Periodic Table of Elements, results in a catalyst composition not only having an enhanced selectivity to lower olefins such as ethylene and/or propylene but also having a longer catalyst lifetime when used in the conversion of feedstocks, such as oxygenates, into olefin(s).

Molecular Sieves

Molecular sieves that may be used herein include silicoaluminophosphates (SAPOs) and aluminophosphates (AlPOs) having an average pore dimension of at least 3 Angstroms and at least one reactive hydroxyl group. Suitable molecular sieves include, but are not limited to the structural types of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, and THO and substituted examples of these structural types, as described in Ch. Baerlocher, W. M. Meier, and D. H. Olson, Atlas of Zeolite Framework Types, fifth edition (Elsevier, 2001), incorporated herein by reference.

Silicoaluminophosphate (SAPO) molecular sieves contain a three-dimensional microporous crystalline framework structure of $[SiO_4]$, $[AlO_4]$ and $[PO_4]$ corner sharing tetrahedral units. Synthesis of SAPO molecular sieves, their formulation into catalysts, and their use in converting a hydrocarbon feedstock into olefin(s), particularly where the feedstock is methanol, are disclosed in U.S. Pat. Nos. 4,440,871, 4,499,327, 4,677,242, 4,677,243, 4,873,390, 5,095,163, 5,714,662 and 6,166,282, all of which are herein fully incorporated by reference. Examples of SAPO materials useful herein include SAPO-18, SAPO-34, SAPO-35, SAPO-44, SAPO-47 and SAPO-56, particularly SAPO-34, intergrowths o f SAPO-34 and SAPO-18, and mixtures thereof.

Aluminophosphate molecular sieves contain a three-dimensional microporous crystalline framework structure of $[AlO_4]$ and $[PO_4]$ corner sharing tetrahedral units. A detailed description of the background and synthesis of aluminophosphates is found in U.S. Pat. No. 4,310,440, which is incorporated herein by reference in its entirety. Examples of AlPO materials useful herein include AlPO-18 and AlPO-34.

The SAPOs and AlPOs used herein typically have pore windows defined 8-membered rings of tetrahedrally coordinated atoms and an average pore dimension less than or equal to about 5 Å, such as in the range of from about 3 Å to about 5 Å, for example from about 3 Å to about 4.5 Å, and particularly from about 3.5 Å to about 4.3 Å. The term "average pore dimension" is used herein in its commonly accepted sense, such that, for a microporous material with pore dimensions of X Angstrom by Y Angstrom, the average pore dimension is (X+Y)/2 Angstrom.

The SAPOs and AlPOs used herein can also include a metal component, for example as substituent in the framework of the molecular sieve. For example, the metal component can be is an alkali metal of Group 1 of the Periodic Table of Elements, an alkaline earth metal of Group 2 of the Periodic Table of Elements, a rare earth metal of Group 3 of the Periodic Table of Elements, including the Lanthanides: lanthanum, cerium, praseodymium, neodymium, samarium, europium, gadolinium, terbium, dysprosium, holmium, erbium, thulium, ytterbium and lutetium; and scandium or yttrium, a transition metal of Groups 4 to 12 of the Periodic Table of Elements, or mixtures of any of these metal species. Typically, the metal is selected from the group consisting of Co, Cr, Cu, Fe, Ga, Ge, Mg, Mn, Ni, Sn, Ti, Zn and Zr, and mixtures thereof.

In general, the molecular sieve employed herein can be represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and has a value from 0 to 1, preferably 0 to 0.5, and most preferably from 0 to 0.3; x, y, and z represent the mole fraction of Al, P and M as tetrahedral oxides, where M is a metal selected from one of Groups 1, 2, 3, 4, 5, 6, 7, 8, 9, 10, 11, 12, 13, 14 and Lanthanide's of the Periodic Table of Elements, preferably M is selected from one of the group consisting of Si, Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Molecular Sieve Synthesis

Generally, AlPO and SAPO molecular sieves are synthesized by the hydrothermal crystallization of one or more of a source of aluminum, a source of phosphorus, a source of silicon and a templating agent, such as a nitrogen containing organic compound. Typically, a combination of sources of silicon, aluminum and phosphorus, optionally with one or more templating agents, is placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting.

Non-limiting examples of silicon sources include silicates, fumed silica, for example, Aerosil-200 available from Degussa Inc., New York, N.Y., and CAB-O-SIL M-5, organosilicon compounds such as tetraalkyl orthosilicates, for example, tetramethyl orthosilicate (TMOS) and tetraethylorthosilicate (TEOS), colloidal silicas or aqueous suspensions thereof, for example Ludox HS-40 sol available from E.I. du Pont de Nemours, Wilmington, Del., silicic acid or any combination thereof.

Non-limiting examples of aluminum sources include aluminum alkoxides, for example aluminum isopropoxide, aluminum phosphate, aluminum hydroxide, sodium aluminate, pseudo-boehmite, gibbsite and aluminum trichloride, or any combination thereof. A convenient source of aluminum is pseudo-boehmite, particularly when producing a silicoaluminophosphate molecular sieve.

Non-limiting examples of phosphorus sources, which may also include aluminum-containing phosphorus compositions, include phosphoric acid, organic phosphates such as triethyl phosphate, and crystalline or amorphous aluminophosphates such as $AlPO_4$, phosphorus salts, or combinations thereof. A convenient source of phosphorus is phosphoric acid, particularly when producing a silicoaluminophosphate.

Templating agents are generally compounds that contain elements of Group 15 of the Periodic Table of Elements, particularly nitrogen, phosphorus, arsenic and antimony. Typical templating agents also contain at least one alkyl or aryl group, such as an alkyl or aryl group having from 1 to 10 carbon atoms, for example from 1 to 8 carbon atoms. Preferred templating agents are often nitrogen-containing compounds, such as amines, quaternary ammonium compounds and combinations thereof. Suitable quaternary ammonium compounds are represented by the general formula $R_4N^+$, where each R is hydrogen or a hydrocarbyl or substituted hydrocarbyl group, preferably an alkyl group or an aryl group having from 1 to 10 carbon atoms.

Non-limiting examples of templating agents include tetraalkyl ammonium compounds including salts thereof, such as tetramethyl ammonium compounds, tetraethyl ammonium compounds, tetrapropyl ammonium compounds, and tetrabutylammonium compounds, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo[2,2,2]octane, N,N,N',N'-tetramethyl-1,6-hexanediamine, N-methyldiethanolamine, N-methyl-ethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo[2,2,2]octane ion; di-n-butylamine, neopentylamine, di-n-pentylamine, isopropylamine, t-butyl-amine, ethylenediamine, pyrrolidine, and 2-imidazolidone.

The pH of the synthesis mixture containing at a minimum a silicon-, aluminum-, and/or phosphorus-composition, and a templating agent, is generally in the range of from 2 to 10, such as from 4 to 9, for example from 5 to 8.

Generally, the synthesis mixture described above is sealed in a vessel and heated, preferably under autogenous pressure, to a temperature in the range of from about 80° C. to about 250° C., such as from about 100° C. to about 250° C., for example from about 125° C. to about 225° C., such as from about 150° C. to about 180° C.

The time required to form the crystalline product is usually dependent on the temperature and can vary from immediately up to several weeks. Typically the crystallization time is from about 30 minutes to around 2 weeks, such as from about 45 minutes to about 240 hours, for example from about 1 hour to about 120 hours. The hydrothermal crystallization may be carried out with or without agitation or stirring. The crystallization may be aided by the addition of seeds from another or the same framework type molecular sieve.

Once the crystalline molecular sieve product is formed, usually in a slurry state, it may be recovered by any standard technique well known in the art, for example, by centrifugation or filtration. The recovered crystalline product may then be washed, such as with water, and then dried, such as in air.

Where a templating agent is used in the synthesis of the molecular sieve, any templating agent retained in the product may be removed after crystallization and prior to treatment with the organometallic compound by numerous well known techniques, for example, by calcination. Calcination involves contacting the molecular sieve containing the templating agent with a gas, preferably containing oxygen, at any desired concentration at an elevated temperature sufficient to either partially or completely remove the templating agent. Typically, the molecular sieve is calcined at a temperature of at least about 300° C., such as at least about 450° C., for example at least about 550° C. and at a temperature of at most about 800° C., such as at most about 750° C., and for example at most about 700° C. The molecular sieve is calcined for a period of time of at least about 1 hour, typically at least about 2 hours, for example at least about 3 hours and for a period of time of at most about 24 hours, typically at most about 12 hours, and for example at most about 10 hours.

Organometallic Reagent Modification

The organometallic compound used herein is defined as a compound having at least one metal bound to at least one alkyl group. The alkyl group is typically linear and may have up to at most about twenty (20) carbon atoms, such as at most about twelve (12) carbon atoms, for example at most about six (6) carbon atoms.

Metals useful in the organometallic compound are selected from the group consisting of Group 1 to Group 14, and mixtures thereof. See *The Chemistry of the Elements*, Second Edition, 1998. Suitable metals include, but are not limited to, lithium, gallium, germanium, magnesium, zinc, and mixtures thereof.

Suitable organometallic compounds include, but are not limited to, methyl lithium, butyl lithium, dimethyl zinc, diethyl zinc, ethylmagnesium bromide, methylmagnesium bromide, methylmagnesium chloride, trimethyl gallium, triethyl gallium, tetraethyl germanium, and tetramethyl germanium and mixtures thereof. Dimethyl zinc is one particularly suitable organometallic compound. In general, the organometallic compound should have a kinetic diameter less than the average pore dimension of the molecular sieve so that the organometallic compound can access the internal hydroxyl groups of the sieve.

The molecular sieve is treated with organometallic compound by contacting the sieve with a solution containing the organometallic compound and a non-proton donating solvent. The concentration of organometallic compound in the solution is typically at least about 0.001 M, such as at least about 0.005 M, for example at least about 0.01 M. The concentration of organometallic compound in the solution is typically at most about 10.0 M, such as at most about 5.0 M, for example at most about 3.0 M.

Suitable non-proton donating solvents (anhydrous grade) include, but are not limited to, linear or branched alkanes or alkenes having a carbon number between five (5) and twenty (20), such as heptane; halogen-substituted alkanes having more than one (1) carbon, where the halogen can be fluorine or chlorine; ethers; ketones; sulfoxides; heterocyclic compounds, such as tetrahydrofuran, substituted pyridine or unsubstituted pyridine; aromatic compounds, such as benzene, toluene, or xylenes; and mixtures thereof.

The organometallic compound containing solution is contacted, under an inert atmosphere such as $N_2$, with the molecular sieve, with or without stirring, under autogenous pressure in a reaction vessel. The reaction mixture may or may not be heated and is typically at a temperature of at least about −40° C., such as at least about −25° C., for example at least about 0° C. and at a temperature of at most about 200° C., such as at most about 150° C., for example at most about 100° C.

The organometallic compound is contacted with the molecular sieve for a sufficient period of time depending upon the process temperature, the pressure, the type of organometallic compound solution used, the concentration of the organometallic compound in solution, and the type of molecular sieve used. Generally, the reaction is allowed to take place for several hours. The reaction takes place for a time of at least about 1 hour, such as at least about 2 hours, for example at least about 3 hours and for a time of at most 48 hours, such as at most about 24 hours, for example at most about 20 hours.

The organometallic treated molecular sieve is then separated from the non-proton donating solvent, for example by fitration. The separated molecular sieve may then be washed with one or more organic solvents to remove traces of unreacted or loosely bound organometallic compound. Suitable organic solvents include, but are not limited to, methanol, ethanol, 2-propanol, diethyl ether, acetone, hexane, heptane, tetrahydrofuran, and toluene. The washed molecular sieve can then be dried, for example at 110° C. overnight.

The amount of metal disposed into or onto, or within the pores of the organometallic modified molecular sieve is such that the molecular sieve comprises at least about 0.05 percent by weight metal, such as at least about 0.5 percent by weight metal, for example at least about 1.0 percent by weight metal and at most about 20 percent by weight metal, such as at most about 10 percent by weight metal, and for example at most about 8 percent by weight metal.

The organometallic treated molecular sieve can be further contacted with a solution of the same or different organometallic compound according to the method of the present invention. Multiple cycles of contacting the organometallic solution with the molecular sieve can be carried out, if required, to achieve the desired degree of metal loading.

After the organometallic treatment, the resultant metal species is disposed into, onto, or within the molecular sieve. The metal species is introduced through chemical reactions with the hydroxyl groups of the molecular sieve, wherein the metal species is bound to the oxygen atom of the reactive hydroxyl group and is disposed within the pores, on the internal surfaces of the molecular sieve, and/or on the external surfaces of the molecular sieve. Under the conditions used according to the method of the present invention, the alkyl group of the organometallic compound reacts with the hydroxyl groups forming an alkane, such as methane or ethane, and the metal species is attached to the oxygen atoms at the sites of the reactive hydroxyl groups, either within the pores, at the internal and/or external surfaces of the molecular sieve.

After the organometallic treated molecular sieve is washed and dried, the molecular sieve may be calcined or partially calcined. Typically, the molecular sieve of the invention is calcined, with or without oxygen, prior to use, for example, in a conversion reactor. The organometallic treated molecular sieve is typically calcined at a temperature of at least about 300° C., such as at least about 450° C., for example at least about 550° C. and at a temperature of at most about 800° C., such as at most about 750° C., and for example at most about 700° C. The calcination is typically conducted for a period of time of at least about 1 hour, such as at least about 2 hours, for example at least about 3 hours and for a period of time of at most about 24 hours, such as at most about 12 hours and for example at most about 10 hours.

Optional Metal Oxide

In addition to the treatment with an organometallic compound, the molecular sieve used herein can be combined with one or more active metal oxides. The active metal oxides useful herein are those metal oxides, different from typical binders and/or matrix materials, that, when used in combination with the treated molecular sieve, are effective in extending of the useful life of the molecular sieve, particularly when used in the conversion of oxygenates to olefins. Suitable active metal oxides are those metal oxides having a Group 4 metal (such as zirconium and/or hafnium), a Group 2 metal (for example magnesium, calcium, strontium and barium) and/or a Group 3 metal, including the Lanthanides and Actinides, (for example yttrium, scandium, lanthanum, cerium, praseodymium, neodymium, samarium and thorium). In one embodiment, the active Group 4 metal oxide is an active zirconium metal oxide, either alone or in combination with calcium oxide, lanthanum oxide and/or yttrium oxide. In general, oxides of silicon, aluminum, and combinations thereof are not preferred.

In particular, the metal oxides useful herein have an uptake of carbon dioxide at 100° C. of at least 0.03 mg/m$^2$ of the metal oxide. Although the upper limit on the carbon dioxide uptake of the metal oxide is not critical, in general the metal oxides useful herein will have a carbon dioxide at 100° C. of less than 10 mg/m$^2$ of the metal oxide, such as less than 5 mg/m$^2$ of the metal oxide.

In order to determine the carbon dioxide uptake of a metal oxide, the following procedure is adopted using a Mettler TGA/SDTA 851 thermogravimetric analysis system under ambient pressure. A sample of the metal oxide is dehydrated in flowing air to about 500° C. for one hour. The temperature of the sample is then reduced in flowing helium to 100° C. After the sample has equilibrated at the desired adsorption temperature in flowing helium, the sample is subjected to 20 separate pulses (about 12 seconds/pulse) of a gaseous mixture comprising 10-weight % carbon dioxide with the remainder being helium. After each pulse of the adsorbing gas the metal oxide sample is flushed with flowing helium for 3 minutes. The increase in weight of the sample in terms of mg/mg adsorbent based on the adsorbent weight after treatment at 500° C. is the amount of adsorbed carbon dioxide. The surface area of the sample is measured in accordance with the method of Brunauer, Emmett, and Teller (BET) published as ASTM D 3663 to provide the carbon dioxide uptake in terms of mg carbon dioxide/m$^2$ of the metal oxide.

The active metal oxide(s) used herein can be prepared using a variety of methods. It is preferable that the active metal oxide is made from an active metal oxide precursor, such as a metal salt, such as a halide, nitrate sulfate or acetate. Other suitable sources of the metal oxide include compounds that form the metal oxide during calcination, such as oxychlorides and nitrates. Alkoxides are also suitable sources of the metal oxide, for example zirconium n-propoxide. A preferred source of the Group 4 metal oxide is hydrated zirconia. The expression, hydrated zirconia, is intended to connote a material comprising zirconium atoms covalently linked to other zirconium atoms via bridging oxygen atoms, and further comprising available hydroxyl groups.

In one embodiment, the active metal oxide is prepared by hydrothermal treatment under conditions that include a temperature of at least 80° C., such as at least 100° C. The hydrothermal treatment typically takes place in a sealed vessel at greater than atmospheric pressure, although the treatment can also involve the use of an open vessel under reflux conditions. Agitation of the metal oxide in a liquid medium, for example, by the action of refluxing liquid and/or stirring, promotes the effective interaction of the oxide with the liquid medium. The duration of the contact of the oxide with the liquid medium is conveniently at least 1 hour, such as at least 8 hours. The liquid medium for this treatment typically has a pH of about 7 or greater, such as 9 or greater. Non-limiting examples of suitable liquid media include water, hydroxide solutions (including hydroxides of $NH_4^+$, $Na^+$, $K^+$, $Mg^{2+}$, and $Ca^{2+}$), carbonate and bicarbonate solutions (including carbonates and bicarbonates of $NH_4^+$, $Na^+$, $K^+$, $Mg^{2+}$, and $Ca^{2+}$), pyridine and its derivatives, and alkyl/hydroxyl amines.

In another embodiment, the active metal oxide is prepared, for example, by subjecting a liquid solution, such as an aqueous solution, comprising a source of ions of the desired metal to conditions sufficient to cause precipitation of a hydrated precursor of the solid oxide material, such as by the addition of a precipitating reagent to the solution. For example, the precipitating agent may be a base such as sodium hydroxide or ammonium hydroxide.

When a mixture of a Group 4 metal oxide with a Group 2 and/or 3 metal oxide is to be prepared, a first liquid solution comprising a source of ions of a Group 4 metal can be combined with a second liquid solution comprising a source of ions of a Group 2 and/or Group 3 metal. This combination of two solutions can take place under conditions sufficient to cause co-precipitation of a hydrated precursor of the mixed oxide material as a solid from the liquid medium. Alternatively, the source of ions of the Group 4 metal and the source of ions of the Group 2 and/or Group 3 metal may be combined into a single solution. This solution may then be subjected to conditions sufficient to cause co-precipitation of a hydrated precursor of the solid mixed oxide material, such as by the addition of a precipitating reagent to the solution.

The temperature at which the liquid medium is maintained during the precipitation is typically less than or equal to about 200° C., such as in the range of from about 0° C. to about 200° C. A particular range of temperatures for precipitation is from about 20° C. to about 100° C. The resulting gel is then hydrothermally treated at temperatures of at least 80° C., such as at least 100° C. The hydrothermal treatment typically takes place in a vessel at atmospheric pressure. The gel, in one embodiment, is hydrothermally treated for up to 10 days, such as up to 5 days, for example up to 3 days.

The hydrated precursor of the metal oxide(s) is then recovered, for example by filtration or centrifugation, and washed and dried. The resulting material can then be calcined, such as in an oxidizing atmosphere, at a temperature of at least 400° C., such as at least 500° C., for example from about 600° C. to about 900° C., and particularly from about 650° C. to about 800° C., to form the active metal oxide or active mixed metal oxide. The calcination time is typically up to 48 hours, such as for about 0.5 to about 24 hours, for example for about 1.0 to about 10 hours. In one embodiment, calcination is carried out at about 700° C. for about 1 to about 3 hours.

The resulting active metal oxide is then physically mixed with the molecular sieve, normally after the sieve has been treated with the organometallic compound. Normally, the molecular sieve and active metal oxides are intimately mixed in their calcined state. Intimate mixing can be achieved by any method known in the art, such as mixing with a mixer muller, drum mixer, ribbon/paddle blender, kneader, or the like. Chemical reaction between the molecular sieve and the metal oxide(s) is unnecessary and, in general, is not preferred.

Typically, the weight ratio of the molecular sieve to the active metal oxide(s) is in the range of from about 5 weight percent to about 800 weight percent, such as from about 10 weight percent to about 600 weight percent, particularly from about 20 weight percent to about 500 weight percent, and more particularly from about 30 weight percent to about 400 weight percent.

Catalyst Composition

The organometallic treated molecular sieves of the present invention are useful as catalyst compositions in the conversion of feedstocks containing at least one organic compound having at least one oxygen atom (hereinafter referred to as an oxygenate) into light olefins. For this purpose, the silicoaluminophosphates may be used in combination or in admixture with other components. Materials which can be blended with the molecular sieve can be various inert or catalytically active materials, such as binder and matrix materials. Where the organometallic treated molecular sieve is combined with one or more active metal oxides, the binder and/or matrix material is different from the active metal oxide(s).

There are many different binders that are useful in forming catalyst compositions. Non-limiting examples of binders that are useful alone or in combination include various types of hydrated alumina, silicas, and/or other inorganic oxide sols. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide binder component. For example, an alumina sol will convert to an aluminum oxide binder following heat treatment.

Matrix materials are typically effective in reducing overall catalyst cost, acting as thermal sinks to assist in shielding heat from the catalyst composition for example during regeneration, densifying the catalyst composition, and increasing catalyst strength such as crush strength and attrition resistance. Non-limiting examples of matrix materials include beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include subbentonites and those kaolins known as, for example, Dixie, McNamee, Georgia and Florida clays. Non-limiting examples of other matrix materials include haloysite, kaolinite, dickite, nacrite, or anauxite. The matrix material, such as a clay, may be subjected to well known modification processes such as calcination and/or acid treatment and/or chemical treatment. Where the catalyst composition contains a binder or matrix material, the catalyst composition typically contains from about 1% to about 90%, such as from about 2% to about 80%, and particularly from about 5% to about 60%, by weight of the molecular sieve based on the total weight of the catalyst composition.

Where the catalyst composition contains a binder and a matrix material, the weight ratio of the binder to the matrix material is typically from 1:15 to 1:5, such as from 1:10 to 1:4, and particularly from 1:6 to 1:5. The amount of binder is typically from about 2% by weight to about 30% by weight, such as from about 5% by weight to about 20% by weight, and particularly from about 7% by weight to about 15% by weight, based on the total weight of the binder, the molecular sieve and matrix material.

Additional molecular sieve materials can be included as a part of the catalyst composition. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include LEV, MFI, MEL, MTW, EUO, MTT, HEU, FER, AFO, AEL, TON, and substituted forms thereof. These small and medium pore molecular sieves are described in greater detail in the *Atlas of Zeolite Framework Types*, which is previously incorporated herein by reference. Preferred molecular sieves which can be used in combination with the present organometallic treated catalyst include ZSM-5, ZSM-34, urinate, levyne and chabazite.

The catalyst particles generally have a size of at least about 20μ, such as at least about 30μ, for example at least about 50μ. The catalyst particles generally have a size of at most about 3,000μ, such as at most about 200μ, and for example at most about 150μ. The catalyst particles can be subjected to a variety of treatments to achieve the desired physical and chemical characteristics. Such treatments include, but are not necessarily limited to hydrothermal treatment, calcination, acid treatment, base treatment, milling, ball milling, grinding, spray drying, and combinations thereof.

Process for Using the Organometallic Treated Molecular Sieve

The organometallic treated molecular sieve according to the present invention and catalyst compositions containing the same are useful for hydrocarbon conversion and in particular for the catalytic conversion of feedstocks, such as oxygenate-containing feedstocks, to light olefins.

In such a process, a feedstock containing at least one oxygenate, and optionally a diluent or a hydrocarbon added separately or mixed with the oxygenate, is contacted with a catalyst containing a treated SAPO molecular sieve in a reaction zone. Another part of the reaction system may be a regenerator, where carbonaceous deposits (or coke) on the catalyst resulting from the oxygenate conversion reaction are removed by contacting the catalyst with regeneration medium.

The oxygenate feedstock comprises at least one organic compound which contains at least one oxygen atom (oxygenate), such as aliphatic alcohols, ethers, carbonyl compounds (aldehydes, ketones, carboxylic acids, carbonates, esters and the like). Examples of suitable oxygenate compounds include, but are not limited to, $C_1$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Representative alcohols include lower ($C_1$–$C_4$) straight and branched chain aliphatic alcohols and their unsaturated counterparts. Particularly suitable oxygenate compounds are methanol, dimethyl ether and mixtures thereof.

The method of making the preferred olefin product in this invention can include the additional step of making the oxygenate feedstock from hydrocarbons such as oil, coal, tar sand, shale, biomass and natural gas. Methods for making the oxygenates are known in the art. These methods include fermentation to alcohol or ether, making synthesis gas, then converting the synthesis gas to alcohol or ether. Synthesis gas can be produced by known processes such as steam reforming, autothermal reforming and partial oxidization.

One or more inert diluents may be present in the feedstock, for example, in an amount of from 1 to 99 molar percent, based on the total number of moles of all feed and diluent components fed to the reaction zone (or catalyst). As defined herein, diluents are compositions which are essentially non-reactive across a molecular sieve catalyst, and primarily function to make the oxygenates in the feedstock less concentrated. Typical diluents include, but are not necessarily limited to helium, argon, nitrogen, carbon monoxide, carbon dioxide, water, essentially non-reactive paraffins (especially the alkanes such as methane, ethane, and propane), essentially non-reactive alkylenes, essentially non-reactive aromatic compounds, and mixtures thereof. Particularly suitable diluents are water and nitrogen. Water can be injected in either liquid or vapor form.

Hydrocarbons can also be included as part of the feedstock, i.e., as co-feed. As defined herein, hydrocarbons included with the feedstock are hydrocarbon compositions which are converted to another chemical arrangement when contacted with the molecular sieve catalyst. These hydrocarbons can include olefins, reactive paraffins, reactive alkylaromatics, reactive aromatics or mixtures thereof. Suitable hydrocarbon co-feeds include propylene, butylene, pentylene, $C_4^+$ hydrocarbon mixtures, $C_5^+$ hydrocarbon mixtures, and mixtures thereof. Typical co-feeds are $C_4^+$ hydrocarbon mixtures and, in particular, the $C_4^+$ hydrocarbon mixtures which are obtained from separation and recycle of reactor product.

Generally, the oxygenate feed is contacted with the catalyst when the oxygenate is in the vapor phase, although the process may also be carried out in the liquid or a mixed vapor/liquid phase.

The process can generally be carried out at a wide range of temperatures. Typically, the operating temperature is at least about 200° C., such as at least about 300° C., for example at least about 350° C. and the temperature is at most about 700° C., such as at most about 650° C., for example at most about 600° C. At the lower end of the temperature range, the formation of the desired olefin products may become markedly slow. At the upper end of the temperature range, the process may not form an optimum amount of product.

The pressure also may vary over a wide range, including autogenous pressures. Effective pressures may include, but are not necessarily limited to, oxygenate partial pressures of at least 1 psia (6.9 kPa), such as at least 5 psia (34.5 kPa). The process is particularly effective at higher oxygenate partial pressures, such as an oxygenate partial pressure of greater than 20 psia (137.9 kPa), such as at least about 25 psia (172.4 kPa), for example at least about 30 psia (206.8 kPa). For practical design purposes it may be desirable to operate at a methanol partial pressure of not greater than about 500 psia (3447.4 kPa), such as not greater than about 400 psia (2757.9 kPa), for example not greater than about 300 psia (2068.4 kPa).

Generally, the oxygenate feedstock is contacted with the molecular sieve catalyst at a weight hourly space velocity (WHSV) of at least about 1 hr$^{-1}$, such as in the range of from about 1 hr$^{-1}$ to 1000 hr$^{-1}$, for example in the range of from about 20 hr$^{-1}$ to 1000 hr$^{-1}$, and conveniently in the range from about 20 hr$^{-1}$ to 500 hr$^{-1}$. WHSV is defined herein as the weight of oxygenate, and hydrocarbon which may optionally be in the feed, per hour per weight of the molecular sieve content of the catalyst. Because the catalyst or the feedstock may contain other materials which act as inerts or diluents, the WHSV is calculated on the weight basis of the oxygenate feed, and any hydrocarbon which may be present, and the molecular sieve contained in the catalyst.

The conversion of oxygenates to produce light olefins may be carried out in a variety of catalytic reactors. Reactor types include fixed bed reactors, fluid bed reactors, and concurrent riser reactors as described in "Free Fall Reactor", *Fluidization Engineering*, D. Kunii and O. Levenspiel, Robert E. Krieger Publishing Co. NY, 1977, expressly incorporated herein by reference. Additionally, countercurrent free fall reactors may be used in the conversion process as described in U.S. Pat. No. 4,068,136 and "Riser Reactor", *Fluidization and Fluid-Particle Systems*, pages 48–59, F. A. Zenz and D. F. Othmo, Reinhold Publishing Corp., NY 1960, the detailed descriptions of which are also expressly incorporated herein by reference.

In the process of this invention, coked catalyst can be regenerated by contacting with a regeneration medium to remove all or part of the coke deposits. This regeneration can occur periodically within the reactor by ceasing the flow of feed to the reactor, introducing a regeneration medium, ceasing flow of the regeneration medium, and then reintroducing the feed to the fully or partially regenerated catalyst. Regeneration may also occur periodically or continuously outside the reactor by removing at least a portion of the deactivated catalyst to a separate regenerator, regenerating the coked catalyst in the regenerator, and subsequently reintroducing the regenerated catalyst to the reactor. Regeneration can occur at times and conditions appropriate to maintain a desired level of coke on the entire catalyst within the reactor. In one embodiment of continuous operation, only a portion of the catalyst is removed from the reactor and sent to the regenerator to remove the accumulated coke deposits that result during the catalytic reaction.

In the regenerator, the catalyst is contacted with a regeneration medium containing oxygen or other oxidants. Examples of other oxidants include $O_3$, $SO_3$, $N_2O$, NO, $NO_2$, $N_2O_5$, and mixtures thereof. It is preferred to supply $O_2$ in the form of air. The air can be diluted with nitrogen, $CO_2$, or flue gas, and steam may be added. Desirably, the $O_2$ concentration in the regenerator is reduced to a controlled level to minimize overheating or the creation of hot spots in the spent or deactivated catalyst. The deactivated catalyst also may be regenerated reductively with $H_2$, CO, mixtures thereof, or other suitable reducing agents. A combination of oxidative regeneration and reductive regeneration can also be employed.

In essence, the coke deposits are removed from the catalyst during the regeneration process, forming a regenerated catalyst. The regenerated catalyst is then returned to the reactor for further contact with feed. Typical regeneration temperatures are in the range of 250–700° C., such as in the range of 350–700° C., for example in the range of 450–700° C.

In one embodiment, the reactor and regenerator are configured such that the feed contacts the regenerated catalyst before it is returned to the reactor. In an alternative embodiment, the reactor and regenerator are configured such that the feed contacts the regenerated catalyst after it is returned to the reactor. In yet another embodiment, the feed stream can be split such that feed contacts regenerated catalyst before it is returned to the reactor and after it has been returned to the reactor.

It is preferred that the catalyst within the reactor have an average level of coke effective for selectivity to ethylene and/or propylene. Typically, the average coke level on the catalyst will be from about 2 wt. % to about 30 wt. %, such as from about 2 wt. % to about 20 wt. %.

In order to make up for any catalyst loss during the regeneration or reaction process, fresh catalyst can be added. Preferably, the fresh catalyst is added to the regenerated catalyst after it is removed from the regenerator, and then both are added to the reactor. However, the fresh catalyst can be added to the reactor independently of the regenerated catalyst.

When used in the conversion of oxygenates to olefins, the organometallic treated molecular sieve of the invention typically produces an olefin product having an ethylene to propylene ratio of at least about 0.90, such as at least about 0.95, for example at least about 0.98.

It will be appreciated that the olefins produced by the oxygenate-to-olefin conversion reaction of the present invention can be polymerized to form polyolefins, particularly polyethylene and polypropylene. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred polyolefin-forming catalyst is a metallocene catalyst. The preferred temperature range of operation is between 50 and 240° C. and the reaction can be carried out at low, medium or high pressure, being anywhere within the range of about 1 to 200 bars. For processes carried out in solution, an inert diluent can be used, and the preferred operating pressure range is between 10 and 150 bars, with a preferred temperature range of between 120 and 230° C. For gas phase processes, it is preferred that the temperature generally be within a range of 60 to 160° C., and that the operating pressure be between 5 and 50 bars.

In addition to polyolefins, numerous other olefin derivatives may be formed from the olefins produced by the present process. These include, but are not limited to, aldehydes, alcohols, acetic acid, linear alpha olefins, vinyl acetate, ethylene dichloride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore, are not discussed herein.

This invention will be better understood with reference to the following examples, which are intended to illustrate specific embodiments within the overall scope of the invention as claimed.

EXAMPLE 1

Synthesis of SAPO-34

SAPO-34 is made by hydrothermal crystallization of a mixture containing water, a silica source, an alumina source, a phosphorus source, as well as tetraethylammonium hydroxide (TEAOH) and dipropyl amine (DPA) as the templating agents. The resultant SAPO-34 (Sample X) is then calcined in air at 600° C. for 3 hours to remove the template(s) and stored at 200° C. before use. The solid obtained after calcination is hereinafter referred to as Sample Y.

EXAMPLE 2

Dimethyl Zinc Treatment for SAPO-34

Under an $N_2$ atmosphere, 1.6 g of SAPO-34 (Sample Y) is suspended in 50 ml of anhydrous heptane in a 100-ml round-bottom flask. Dimethyl zinc, 0.90 ml of 1.0 M solution in heptane, is slowly added to the mixture via a gas-tight syringe. The starting ratio of zinc to silicon in the SAPO-34 is 0.50. The mixture is stirred at room temperature for 20 hr and centrifuged. The isolated solid is then stirred in 50 ml of anhydrous methanol for 4 hr at room temperature, centrifuged, and dried at 105° C. for one day. The solid is calcined at 600° C. for 3 hr before use and hereinafter referred to as Sample A.

EXAMPLE 3

Dimethyl Zinc Treatment for SAPO-34

The process of Example 2 is repeated but using 2.8 g of SAPO-34 (Sample Y) suspended in 50 ml of anhydrous heptane and 0.84 ml of 1.0 M solution of dimethyl zinc in heptane. The starting ratio of zinc to silicon in the SAPO-34 is 0.25. The solid resulting from calcination at 600° C. for 3 hr is hereinafter referred to as Sample B.

EXAMPLE 4

Dimethyl Zinc Treatment for SAPO-34

The process of Example 2 is repeated but using 2.2 g of SAPO-34 (Sample Y) suspended in 50 ml of anhydrous heptane and 1.40 ml of 1.0 M solution of dimethyl zinc in heptane. The starting ratio of zinc to silicon in the SAPO-34 is 0.60. The solid resulting from calcination at 600° C. for 3 hr is hereinafter referred to as Sample C.

EXAMPLE 5

Dimethyl Zinc Treatment for SAPO-34

The process of Example 2 is repeated but using 1.6 g of SAPO-34 (Sample Y) suspended in 50 ml of anhydrous heptane and 3.50 ml of 1.0 M solution of dimethyl zinc in heptane. The starting ratio of zinc to silicon in the SAPO-34 is 2.00. The solid resulting from calcination at 600° C. for 3 hr is hereinafter referred to as Sample D.

EXAMPLE 6

Dimethyl Zinc Treatment for SAPO-34

The process of Example 2 is repeated but using 4.2 g of SAPO-34 (Sample Y) suspended in 150 ml of anhydrous heptane in a 500-ml round-bottom flask and 50.00 ml of 1.0 M solution of dimethyl zinc in heptane. The starting ratio of zinc to silicon in the SAPO-34 is 9.00. The solid resulting from calcination at 600° C. for 3 hr is hereinafter referred to as Sample E.

COMPARATIVE EXAMPLE 7

Framework Incorporated Zinc SAPO-34

Framework incorporated zinc SAPO-34 is prepared hydrothermally by adding zinc acetate to the synthesis gel of SAPO-34 where triethylamine (TEA) is used as the template, following the procedures reported in EP 1143833 A1, which is fully incorporated herein by reference. The resulting solid is hereinafter referred to as Sample F.

COMPARATIVE EXAMPLE 8

Cation Exchange with SAPO-34

3.3 g of SAPO-34 (Sample X) is refluxed with 0.86 g of $Zn(NO_3)_2 \cdot 6H_2O$ in 35 ml of distilled water for 4 hr. The mixture is filtered and dried at 105° C. overnight. The resulting solid is hereinafter referred to as Sample G.

COMPARATIVE EXAMPLE 9

Cation Exchange with SAPO-34

4.0 g of calcined SAPO-34 (Sample Y) is refluxed with 1.00 g of Zn(NO3)2.6H2O in 50 ml of distilled water for 4 hr. The mixture is filtered and dried at 105° C. overnight. The resulting solid is hereinafter referred to as Sample H.

COMPARATIVE EXAMPLE 10

SAPO-34 Impregnation Via Incipient Wetness 4.0 g of SAPO-34 (Sample X) is slowly wetted with a solution of 0.22 g of Zn(NO3)2.6H2O dissolved in 2.0 ml of de-ionized water. The wet mixture is dried at 105° C. overnight. The resulting solid is hereinafter referred to as Sample I.

COMPARATIVE EXAMPLE 11

SAPO-34 Impregnation Via Incipient Wetness 4.0 g of SAPO-34 (Sample X), is slowly wetted with a solution of 0.52 g of Zn(NO3)2.6H2O dissolved in 2.0 ml of de-ionized water. The wet mixture is dried at 105° C. overnight. The resulting solid is hereinafter referred to as Sample J.

EXAMPLE 12

Methylmagnesium Bromide Treatment of SAPO-34

Under an N2 atmosphere, 7.0 g of SAPO-34 (Sample Y) is placed in a 250-ml schlenk flask and chilled with an ice/acetone bath. A volume of 100 ml methylmagnesium bromide solution (0.7 M in 3/1 toluene/tetrahydrofuran (THF)) is cannulated into the flask. The mixture is allowed to warm up to room temperature and stirred at room temperature for 21 hr. The mixture is then filtered under N2, washed with pentane, followed by ether, and dried under vacuum for 4 hr. The dry powder is stirred with 50 ml of anhydrous methanol for 4 hr and centrifuged. The solid is dried under vacuum overnight and calcined at 600° C. for 3 hr before use and hereinafter referred to as Sample K.

EXAMPLE 13

Dimethyl Zinc Treatment for SAPO-34

Under an N2 atmosphere, 23.2 g of SAPO-34 (Sample Y) is suspended in 200 ml of anhydrous heptane in a 500-ml round-bottom flask. Dimethyl zinc, 7.0 ml of 1.0 M solution in heptane, is slowly added to the mixture via a gas-tight syringe. The starting ratio of zinc to silicon in the SAPO-34 is 0.25. The mixture is stirred at room temperature for 20 hr and centrifuged. The isolated solid is dried at 105° C. for one day and hereinafter referred to as Sample L.

EXAMPLE 14

Repetitive Low Dose Dimethyl Zinc Treatment for SAPO-34

Under an N2 atmosphere, 15.4 g of Sample L is suspended in 150 ml of anhydrous heptane in a 500-ml round-bottom flask. Dimethyl zinc, 5.0 ml of 1.0 M solution in heptane, is slowly added to the mixture via a gas-tight syringe to bring the total starting ratio of zinc to silicon in the SAPO-34 to 0.5. The mixture is stirred at room temperature for 20 hr and centrifuged. The isolated solid is dried at 105° C. for one day and hereinafter referred to as Sample M.

EXAMPLE 15

Repetitive Low Dose Dimethyl Zinc Treatment for SAPO-34

Under an N2 atmosphere, 9.7 g of Sample M is suspended in 100 ml of anhydrous heptane in a 250-ml round-bottom flask. Dimethyl zinc, 3.5 ml of 1.0 M solution in heptane, is slowly added to the mixture via a gas-tight syringe to bring the total starting ratio of zinc to silicon in the SAPO-34 to 0.75. The mixture is stirred at room temperature for 20 hr and centrifuged. The isolated solid is dried at 105° C. for one day and hereinafter referred to as Sample N.

EXAMPLE 16

Repetitive Low Dose Dimethyl Zinc Treatment for SAPO-34

Under an N2 atmosphere, 5.2 g of Sample N is suspended in 60 ml of anhydrous heptane in a 250-ml round-bottom flask. Dimethyl zinc, 2.0 ml of 1.0 M solution in heptane, is slowly added to the mixture via a gas-tight syringe to bring the total starting ratio of zinc to silicon in the SAPO-34 to 1.0. The mixture is stirred at room temperature for 20 hr and centrifuged. The isolated solid is dried at 105° C. for one day and hereinafter referred to as Sample O.

EXAMPLE 17

Methane Formation During Dimethyl Zinc Treatment of SAPO-34

Under an N2 atmosphere, 1.2 g of Sample Y is placed in a 50-ml round bottom flask and is evacuated under vacuum. Anhydrous heptane (24 ml) is added. The mixture is stirred under N2, and 1.6 ml of dimethyl zinc solution (1.0 M in heptane) is added via a gas-tight syringe. The level of methane in the head space of the flask is analyzed by gas chromatography (GC) in order to follow the reaction.

FIG. 1 shows the evolution of methane with time after dimethyl zinc is added to SAPO-34. The Y-axis is the GC peak area ratio of methane vs. the solvent heptane (ACH4/AC7H16). It is believed that if dimethyl zinc reacts mostly with the exterior acid sites of SAPO-34 and inadvertent moisture, immediate release of methane will result and the level of methane will rapidly reach its maximum. As shown in FIG. 1, it takes more than three hours for methane to reach its maximum level, indicating that dimethyl zinc diffuses inside the cage of SAPO-34 and reacts mostly with the interior acid sites.

The reaction is stopped and the solid isolated after ACH4/AC7H16 has reached its maximum. The Zn/Si atomic ratio in the isolated solid is 0.73 as determined by elemental analysis (see Example 19 below).

19

EXAMPLE 18

Methane Formation During Methylmagnesium Bromide Treatment of SAPO-34

Under an N2 atmosphere, 1.2 g of Sample Y is suspended in 30 ml of a 3/1 mixture of anhydrous toluene/anhydrous tetrahydrofuran in a 50-ml round bottom flask. A volume of 1.4 ml of methylmagnesium bromide solution (1.4 M in 3/1 toluene/THF) is added to the mixture via a gas tight syringe. The level of methane in the head space of the flask is analyzed by gas chromatography (GC) in order to follow the reaction.

FIG. 2 shows the evolution of methane with time after methylmagnesium bromide is added to SAPO-34. The Y-axis is the GC peak area ratio of methane vs. the solvent tetrahydrofuran (ACH4/ATHF). It is believed that if methylmagnesium bromide reacts mostly with the exterior acid sites of SAPO-34 and inadvertent moisture, immediate release of methane will result and the level of methane will rapidly reach its maximum. As shown in FIG. 2, it takes about two hours for methane level to reach its maximum, indicating that methylmagnesium bromide diffuses inside the cage of SAPO-34 and reacts with the interior acid sites.

The reaction is stopped and the solid isolated after ACH4/ATHF has reached its maximum. The Mg/Si atomic ratio in the isolated solid is 0.43 as determined by elemental analysis (see Example 19 below).

EXAMPLE 19

Elemental Compositions of Modified SAPO-34

Elemental compositions of modified SAPO-34 samples are analyzed by Inductively Coupled Plasma/Atomic Emission Spectroscopy (ICP/AES) and the results are listed below in Table 1 (Samples A–J). Clearly, the amount of zinc incorporated in SAPO-34 can be controlled by varying the reaction stoichiometry between dimethyl zinc and SAPO-34 in Samples A–E. Similarly, the amount of zinc can also be controlled in the impregnated Samples I and J by varying the amount of zinc nitrate used. In contrast, the amount of zinc incorporated is limited in the cation-exchanged Samples G and H.

EXAMPLE 20

Methanol Uptake of Modified SAPO-34

Methanol uptake (expressed as weight percentage of methanol adsorbed by the molecular sieve) is measured gravimetrically and the results are listed below in Table 2. Clearly, samples of SAPO-34 modified with dimethyl zinc or methylmagnesium bromide have reduced methanol uptake, consistent with reduced cage volume after modification.

EXAMPLE 21

MAS $^1$H NMR Measurement of Modified SAPO-34

The Brønsted acid site density of the modified materials is measured by Magic Angle Spinning proton NMR spectroscopy (MAS 1H NMR). The 1H MAS NMR spectra are obtained on a Bruker AMX360 (360.13 MHz for 1H) wide bore spectrometer with a 4-mm (o.d.) MAS probe using 10-kHz spinning, 3.0 ms 90° pulses, a 30 s pulse delay, and 32 scans were collected. The absolute amount of 1H in each sample is determined by directly comparing the experimental spectral area relative to that of an external quantification standard and weight normalized. The external standards and the samples are run back-to-back under identical conditions to minimize any effects due to the spectrometer instability. The external quantification standard used is octakis(trimethylsiloxy)silesquioxane, more commonly known as Q8M8. Q8M8 is a solid at room temperature, has similar tuning characteristics to silicoaluminophosphates, and has a single peak at about 0.3 ppm from tetramethylsilane (TMS). It is commercially available from Strem Chemicals (CAS No. 51777-38-9). Measurements done in quadruplicate on similar systems give a standard deviation of <4% for this methodology. The results for Samples L–O as well as those for comparative Samples F and H are shown in FIG. 3.

FIG. 3 shows that 1) the Brønsted acid site (3.7 ppm) density decreases proportionally with increasing amount of zinc incorporation, a result of increasing degree of dimethyl zinc modification; and 2) a new peak (1.0 ppm) appears in the dimethyl zinc modified samples, which grows proportionally with increasing amount of zinc incorporation. The data are summarized below in Table 3.

In contrast, the peak around 1 ppm is not seen in either Sample F (framework incorporated zinc SAPO-34) or Sample H (Zn2+ cation exchanged SAPO-34). Therefore MAS 1H NMR clearly shows the structural difference between dimethyl zinc modified SAPO-34 and other zinc-containing SAPO-34 wherein zinc is introduced via other methods.

EXAMPLE 22

Conversion of Methanol to Olefins (MTO)

Conversion of methanol to olefins is carried out in a continuous, tubular, stainless steel reactor (i.d.=0.4 cm; l=13 cm). An amount of 0.025–0.05 g of the calcined and pelletized (40–80 mesh) catalyst is loaded along with quartz granules in the center zone of the tube. The catalyst is heated to 450° C. in flowing nitrogen prior to the MTO reaction. The reaction temperature is either 400° C. or 450° C. as indicated in Tables 4–6 below. In all MTO runs, the pressure of the reactor is maintained at 15 psig with the use of a back-pressure regulator. Methanol is fed to the reactor as saturated vapor by bubbling nitrogen through a reservoir of methanol held at 20° C. The effluent from the reactor is analyzed with an HP5890 Series II Plus Gas Chromatograph with a flame ionization detector (FID). In order to compare selectivity of different catalysts, the weight hourly space velocity (WHSV) is adjusted to keep conversion level similar (90–95%). Selectivity is chosen at the conversion level shown. Catalyst lifetime is defined as the amount of methanol fed through the catalyst from the beginning of reaction to the point where about 50% oxygenates are converted. The results are shown below in Tables 4–6.

Shown in Table 4 below are the MTO product selectivity (400° C.) for Samples A, D and K modified according to the method of the present invention. Results for Sample Y are also shown for comparison.

Table 5 below shows MTO product selectivity (450° C.) for Samples B and C modified according to the present invention and comparative Samples F (framework incorporated) and G (cation exchange with template). Results for Sample Y are also shown for comparison.

MTO product selectivity (450° C.) is shown in Table 6 below for comparative Samples H (cation exchange without template), I (impregnation) and J (impregnation). Results for Sample Y are also shown for comparison.

EXAMPLE 23

Conversion of Methanol to Olefins (MTO) at High Pressure

Samples of dimethyl zinc modified SAPO-34 (Sample L–O) have also been tested for MTO reactions in a high-pressure micro-reactor. Typical conditions are: 25 psig, 475° C., and WHSV=100 h−1. The results are listed in Table 7 below. Selectivity shown is the integrated selectivity through the course of the reaction. Catalyst lifetime is defined as the total amount of methanol converted per gram of catalyst from beginning of reaction to a conversion level of about 10%.

The MTO performance results clearly indicate that the organometallic modification results in an increase in selectivity toward ethylene (Samples A–D, L–O). Total ethylene and propylene selectivity also increases with organometallic treatment (Samples A–D).

Framework incorporated ZnSAPO-34 (Sample F) with similar amount of zinc does not show significant advantage in terms of olefin selectivity. In addition, it is far more difficult to regenerate framework zinc than to replace intra-/inter-cage zinc using dimethyl zinc. Cation exchanged SAPO-34 (Samples G and H) that starts with either calcined (without template) or uncalcined (with template) SAPO-34 does not show significant increase in ethylene selectivity either. Impregnation methods such as incipient wetness (Samples I and J) can achieve similar level of zinc to those of dimethyl zinc modification, however the selectivity toward ethylene does not increase as significantly compared to those of the organometallic modification according to the method of the present invention.

EXAMPLE 24

Conversion of Methanol to Olefins (MTO) for Regenerated Catalysts

Deactivated catalyst (Sample B) after methanol-to-olefins conversion according to Example 22 above is regenerated in-situ by passing air through the reactor at 550° C. for two hours. MTO conversion is then resumed under identical conditions used for the fresh catalyst. The results are shown in FIG. 4. Little or no change in performance is observed, indicating good hydrothermal stability for dimethyl zinc modified SAPO-34 (Sample B).

TABLE 1

Elemental composition of modified SAPO-34

| Sample | Metal (M) incorporated | Metal loading (wt. %) | Composition (atomic ratio) | | | | M/Si |
|---|---|---|---|---|---|---|---|
| | | | M | Si | Al | P | |
| Y | None | 0.0 | 0 | 0.142 | 1 | 0.768 | 0 |
| A | Zn | 2.6 | 0.049 | 0.14 | 1 | 0.776 | 0.35 |
| B | Zn | 1.5 | 0.028 | 0.138 | 1 | 0.745 | 0.21 |
| C | Zn | 3.5 | 0.066 | 0.141 | 1 | 0.757 | 0.47 |
| D | Zn | 9.6 | 0.2 | 0.143 | 1 | 0.755 | 1.4 |
| E | Zn | 18.7 | 0.44 | 0.135 | 1 | 0.72 | 3.3 |
| F | Zn | 2.5 | 0.05 | 0.106 | 1 | 1.02 | 0.47 |
| G | Zn | 0.3 | 0.006 | 0.134 | 1 | 0.748 | 0.04 |
| H | Zn | 0.28 | 0.0052 | 0.138 | 1 | 0.751 | 0.04 |
| I | Zn | 1.2 | 0.022 | 0.143 | 1 | 0.767 | 0.15 |
| J | Zn | 3.5 | 0.067 | 0.143 | 1 | 0.763 | 0.47 |
| K | Mg | 1.9 | 0.094 | 0.138 | 1 | 0.748 | 0.68 |

TABLE 2

Methanol uptake of modified SAPO-34

| Sample | Metal (M) incorporated | Methanol uptake (wt %) |
|---|---|---|
| Y | None | 25 |
| A | Zn | 22 |
| D | Zn | 15 |
| E | Zn | 6 |
| G | Zn | 20 |
| K | Mg | 22 |

TABLE 3

MAS $^1$H NMR of dimethyl zinc modified SAPO-34

| Sample | Composition | | | | | Zn loading (wt. %) | Brønsted acid site (3.7 ppm) density (mmole/g) | New peak (1.0 ppm) density (mmole/g) |
|---|---|---|---|---|---|---|---|---|
| | Zn | Si | Al | P | Zn/Si | | | |
| Y | 0 | 0.142 | 1 | 0.768 | 0 | 0.0 | 1.37 | 0 |
| L | 0.03 | 0.149 | 1 | 0.789 | 0.20 | 1.6 | 1.08 | 0.18 |
| M | 0.062 | 0.149 | 1 | 0.781 | 0.42 | 3.2 | 0.88 | 0.26 |
| N | 0.096 | 0.156 | 1 | 0.794 | 0.61 | 4.9 | 0.74 | 0.35 |
| O | 0.152 | 0.174 | 1 | 0.779 | 0.87 | 7.4 | 0.54 | 0.28 |

TABLE 4

MTO performance (400° C.) for ZnMe$_2$ and MeMgBr modified SAPO-34

| Sample | | Y | A | D | K |
|---|---|---|---|---|---|
| M/Si ratio | | 0 | 0.35 | 1.4 | 0.68 |
| Modification | | None | ZnMe$_2$ | ZnMe$_2$ | MeMgBr |
| WHSV (h$^{-1}$) | | 20 | 15 | 2.5 | 10 |
| Conversion (%) | | 97 | 94.2 | 92 | 95 |
| Lifetime (g MeOH fed/g catalyst) | | 16 | 11 | 1.3 | 11.5 |
| Selectivity (wt %) | C$_2^=$ | 33.3 | 37.3 | 49.4 | 32.4 |
| | C$_3^=$ | 44.9 | 41.8 | 33.5 | 45.4 |
| | C$_4^=$ | 13.9 | 10.2 | 7 | 13.3 |
| | CH$_4$ | 0.55 | 1.67 | 3.9 | 0.77 |
| | C$_2$ | 0.82 | 0.97 | 0.26 | 1.39 |
| | C$_3$ | 1.62 | 1.69 | 0.97 | 1.82 |
| | C$_4$ | 0.59 | 0.48 | 0.23 | 0.87 |
| | C$_5$–C$_6$ | 4.6 | 5.92 | 4.8 | 4.5 |
| C$_2^=$/C$_3^=$ | | 0.75 | 0.9 | 1.5 | 0.71 |
| C$_2^=$ + C$_3^=$ | | 78.2 | 79.1 | 82.9 | 77.8 |

TABLE 5

MTO performance (450° C.) for SAPO-34 modified with zinc according to different methods.

| Sample | | Y | B | C | F | G |
|---|---|---|---|---|---|---|
| Zn/Si ratio | | 0 | 0.2 | 0.47 | 0.5 | 0.045 |
| Modification | | None | ZnMe$_2$ | ZnMe$_2$ | Framework incorporated | Cation exchange |
| WHSV (h$^{-1}$) | | 20 | 30 | 15 | 25 | 30 |
| Conversion (%) | | 90 | 92 | 95 | 91 | 90 |
| Lifetime (g MeOH fed/g catalyst) | | 19 | 7 | 5 | 8 | 18 |
| Selectivity (wt %) | C$_2^=$ | 38.5 | 44.5 | 52 | 38.9 | 41.9 |
| | C$_3^=$ | 38.3 | 37.2 | 29.2 | 38.2 | 37.2 |
| | C$_4^=$ | 11.5 | 8.3 | 7.2 | 11.8 | 10.1 |
| | CH$_4$ | 1.1 | 3 | 7.4 | 4 | 2.2 |
| | C$_2$ | 0.9 | 1.1 | 0.5 | 0.9 | 0.3 |
| | C$_3$ | 0.8 | 1.0 | 0.5 | 1.2 | 0.7 |
| | C$_4$ | 0.2 | 0.2 | 0.05 | 0.2 | 0.2 |
| | C$_5$–C$_6$ | 8.6 | 4.6 | 3.1 | 4.8 | 7.2 |
| C$_2^=$/C$_3^=$ | | 1 | 1.2 | 1.8 | 1 | 1.1 |
| C$_2^=$ + C$_3^=$ (wt %) | | 76.8 | 81.7 | 81.2 | 77.1 | 79.2 |

TABLE 6

MTO performance (450° C.) for SAPO-34 modified with zinc according to different methods.

| Sample | | Y | H | I | J |
|---|---|---|---|---|---|
| Zn/Si ratio | | 0 | 0.038 | 0.15 | 0.47 |
| Modification | | None | Cation exchange (w/o template) | Impregnation | Impregnation |
| WHSV (h$^{-1}$) | | 30 | 60 | 30 | 30 |
| Conversion (%) | | 95 | 96 | 95 | 94 |
| Lifetime (g MeOH fed/g catalyst) | | 25 | 12 | 14 | 7 |
| Selectivity (wt %) | C$_2^=$ | 41 | 35.67 | 45.6 | 48.6 |
| | C$_3^=$ | 36.9 | 41.81 | 36.1 | 34.6 |
| | C$_4^=$ | 10.8 | 12.1 | 9.4 | 8.1 |
| | CH$_4$ | 2.2 | 3.36 | 1.8 | 3.4 |
| | C$_2$ | 0.3 | 0.31 | 0.4 | 0.35 |
| | C$_3$ | 0.75 | 1.05 | 0.6 | 0.45 |
| | C$_4$ | 0.14 | 0.14 | 0.12 | 0.1 |
| | C$_5$–C$_6$ | 7.8 | 5.2 | 6 | 4.4 |
| C$_2^=$/C$_3^=$ | | 1.1 | 0.85 | 1.26 | 1.4 |
| C$_2^=$ + C$_3^=$ | | 77.9 | 77.5 | 81.7 | 83.2 |

TABLE 7

MTO performance (25 psig, 475° C.) for SAPO-34 modified with zinc according to the present invention.

| Sample | | Y | L | M | N | O |
|---|---|---|---|---|---|---|
| Zn/Si ratio | | 0 | 0.20 | 0.42 | 0.61 | 0.87 |
| Modification | | None | ZnMe$_2$ | ZnMe$_2$ | ZnMe$_2$ | ZnMe$_2$ |
| WHSV (h$^{-1}$) | | 100 | 100 | 100 | 100 | 100 |
| Lifetime (g MeOH converted/g catalyst) | | 14.3 | 14.6 | 6.34 | 2.4 | 2.1 |
| Selectivity (wt %) | C$_2^=$ | 35.8 | 37.6 | 36.87 | 34.04 | 32.84 |
| | C$_3^=$ | 40.8 | 38.1 | 37.35 | 33.04 | 33.33 |
| | C$_4^=$ | 14.8 | 13.8 | 12.25 | 9.47 | 9.67 |
| | CH$_4$ | 1.44 | 2.14 | 3.05 | 5.61 | 5.89 |
| | C$_2$ | 0.71 | 0.73 | 0.91 | 1.9 | 1.84 |
| | C$_3$ | 1.85 | 1.64 | 2.0 | 3.92 | 3.75 |
| | C$_4$ | 0.0 | 0.02 | 0.15 | 0.49 | 0.42 |
| | C$_5$–C$_6$ | 1.97 | 2.56 | 2.77 | 2.73 | 3.34 |
| C$_2^=$/C$_3^=$ | | 0.88 | 0.99 | 0.99 | 1.03 | 0.99 |
| C$_2^=$ + C$_3^=$ (wt %) | | 76.63 | 75.65 | 74.22 | 67.08 | 66.16 |

EXAMPLE 25

Preparation of Dimethyl Zinc Modified SAPO-34

Under a N2 atmosphere, 3.0 g of calcined SAPO-34 (Sample Y) are suspended in 50 ml of anhydrous heptane in a 100-ml round-bottom flask. Dimethyl zinc, 1.0 ml of 1.0 M solution in heptane, is slowly added to the mixture via a gas-tight syringe. The starting ratio of zinc to silicon in the SAPO-34 is 0.25. The mixture is stirred at room temperature for 24 hr and centrifuged. The isolated solid is dried at 105° C. for one day and hereinafter referred to as Sample P, which has a Zn/Si ratio of 0.22.

EXAMPLE 26

Preparation of Mixed Metal Oxide La/ZrO$_2$

Fifty grams of ZrOC12.8H2O are dissolved with stirring in 300 ml of distilled water. Another solution containing 4.2 grams of La(NO3)3.6H2O and 300 ml of distilled water is prepared. These two solutions are combined with stirring and the pH of the mixture is adjusted to approximately 9 by the addition of concentrated ammonium hydroxide (28.9 grams). The resultant slurry is then put in polypropylene bottles and placed in a steambox (100° C.) for 72 hours. The product formed is recovered by filtration, washed with excess water, and dried overnight at 85° C. A portion of this catalyst is calcined to 700° C. in flowing air for 3 hours to produce a mixed metal oxide containing a nominal 5% La on zirconia.

EXAMPLE 27

Preparation of Catalyst of SAPO-34/ZnMe$_2$ with La/ZrO$_2$

In a drybox filled with N2, 190 mg of SAPO-34/ZnMe2 (Sample P) from Example 25 is mixed with 310 mg of La/ZrO2 from Example 26 by gentle but thorough grinding. The weight ratio of SAPO-34/ZnMe2 to La/ZrO2 is 30/50. The combined catalyst (Sample Q) is calcined at 600° C. under flowing air for 3 hr before use for MTO conversion.

EXAMPLE 28

MTO Conversion

The catalytic performance of the base case catalyst (Sample Y) and of SAPO-34/ZnMe2 sieve, with and without La/ZrO2, are investigated using a pure methanol feed at a temperature of 475° C., a pressure of 25 psig, a WHSV of 100 hr−1 based on sieve. The amount of sieve in the reactor is 20 mg and the bed is diluted with quartz to minimize hot spots in the reactor. For the combined catalyst, the total catalyst load was adjusted based on the sieve content of the composite catalyst such that the amount of sieve in the reactor remained 20 mg and the methanol weight hourly space velocity remained 100 hr−1 based on the amount of molecular sieve in the bed. The results are shown in Tables 8 and 9.

TABLE 8

| Sample | Catalyst Composition | Lifetime (g MeOH/ g sieve) | Prime Olefin % | $C_2^=/C_3^=$ | $C_3$ Purity (%) |
|---|---|---|---|---|---|
| Y | 100% SAPO-34 | 14.3 | 76.63 | 0.88 | 95.66 |
| P | 98% SAPO-34/ 2% Zn(OH)$_x$ | 8 | 76.16 | 0.92 | 95.24 |
| Q* | 37% SAPO-34/ 1% Zn(OH)$_x$/ 62% of 5% La/ZrO$_2$ | 26.4 | 76.78 | 1.05 | 97.07 |

*Data reported are averages of two independent runs

TABLE 9

| Sample | $CH_4$ | $C_2^=$ | $C_2°$ | $C_3^=$ | $C_3°$ | $C_4$'s | $C_5+$ |
|---|---|---|---|---|---|---|---|
| Y | 1.44 | 35.79 | 0.71 | 40.84 | 1.85 | 14.83 | 1.97 |
| P | 2.03 | 36.58 | 0.78 | 39.58 | 1.98 | 13.76 | 2.03 |
| Q* | 2.34 | 39.28 | 0.39 | 37.50 | 1.13 | 11.81 | 4.32 |

*Data reported are averages of two independent runs

In Table 8, "Lifetime" is defined as the cumulative grams of methanol converted per gram of molecular sieve when methanol conversion falls to 10%. If the conversion has not reached 10% by the end of the experiment, lifetime is estimated by linear extrapolation based on the rate of decrease in conversion over the last two data points in the experiment. "Prime Olefin" is the sum of the selectivity to ethylene and propylene. The ratio "C2=/C3=" is the ratio of the ethylene to propylene selectivities weighted over the run. The "C3 Purity" is calculated by dividing the propylene selectivity by the sum of the propylene and propane selectivities. In Table 9, the selectivities for methane, ethylene, ethane, propylene, propane, C4's and C5+ are average selectivities weighted over the run. Note that the C5+'s consist only of C5's, C6's and C7's. The selectivities do not sum to 100% in the Table because these selectivities have been corrected for coke.

The results from Tables 8 and 9 clearly show that the combined catalyst has significant performance advantages over either SAPO-34/ZnMe2 or SAPO-34 alone in that 1) catalyst lifetime is 200% greater than SAPO-34/ZnMe2 and 70% greater than SAPO-34; 2) ethylene to propylene ratio is 15% higher than SAPO-34/ZnMe2 and 20% higher than SAPO-34 alone; 3) total prime olefin selectivity remains constant; 4) selectivity to ethane decreases by 50% vs. SAPO-34/ZnMe2 and 45% vs. SAPO-34; 5) selectivity to produce decreases by 43% vs. SAPO-34/ZnMe2 and 39% vs. SAPO-34. The decrease in selectivity to alkanes suggests hydrogen transfer reactions have been inhibited.

Having now fully described this invention, it will be appreciated by those skilled in the art that the invention can be performed within a wide range of parameters within what is claimed, without departing from the spirit and scope of the invention.

What is claimed is:

1. A method for making an organometallic treated molecular sieve comprising:
   a) providing a molecular sieve having at least [AlO$_4$] and [PO$_4$] tetrahedral units and having an average pore dimension less than or equal to about 5 Å, the molecular sieve having at least one hydroxyl group;
   b) contacting said molecular sieve with a solution comprising an organometallic compound and a non-proton donating solvent, wherein said organometallic compound comprises at least one metal bond to at least one alkyl group;

c) separating the organometallic treated molecular sieve from the solution and;

d) calcining the separated organometallic treated molecular sieve.

2. The method of claim 1, wherein said molecular sieve comprises [SiO_4], [AlO_4] and [PO_4] tetrahedral units.

3. The method of claim 1, wherein said molecular sieve is an alunilnophosphate or a silicoaluminophosphate.

4. The method of claim 1, wherein said molecular sieve is a silicoaluminophosphate.

5. The method of claim 4, wherein said molecular sieve is selected from SAPO-18, SAPO-34, SAPO-35, SAPO-44, SAPO-47, SAPO-56 and inter-growths and mixtures thereof.

6. The method of claim 1, wherein said molecular sieve has an average pore dimension in the range of from 3 Å to about 5 Å.

7. The method of claim 1, wherein said organometallic compound has a kinetic diameter less than the average pore dimension of the molecular sieve.

8. The method of claim 1, wherein said at least one metal of said organometallic compound is selected from zinc, lithium, magnesium, gallium, gennanium, and mixtures thereof.

9. The method of claim 1, wherein said at least one alicyl group has from 1 to 20 carbon atoms.

10. The method of claim 1, wherein said at least one ailcyl group has from 1 to 6 carbon atoms.

11. The method of claim 1, wherein said organometallic compound is selected from methyl lithium, butyl lithium, dimethyl zinc, diethyl zinc, ethylmagnesium bromide, methylmagnesium bromide, methylmagnesium chloride, trimethyl gallium, triethyl gallium, tetraethyl gallium, tetramethylgallium, and mixtures thereof.

12. The method of claim 1, wherein said organometallic compound is dimethyl zinc.

13. The method of claim 1, wherein said organometallic compound is methylmagnesium bromide.

14. The method of claim 1, wherein b) is carried out for at a temperature of about −40° C. to about 200° C. for a period of about 1 hour to about 48 hours.

15. The method of claim 1, wherein b) is carried out for at a temperature of about −25° C. to about 150° C. for a period of about 2 hour to about 24 hours.

16. The method of claim 1, wherein b) is carried out for at a temperature of about 0° C. to about 100° C. for a period of about 3 hour to about 20 hours.

17. The method of claim 1, wherein the concentration of said organometallic compound in said solution is about 0.001 M to about 10 M.

18. The method of claim 1, wherein the concentration of said organometallic compound in said solution is about 0.005 M to about 5 M.

19. The method of claim 1, wherein the concentration of said organometallic compound in said solution is about 0.01 M to about 3 M.

20. The method of claim 1, wherein said non-proton donating solvent is selected from heptane, tetrahydrofuran, benzene, toluene, xylenes, diethyl ether and mixtures thereof.

21. The method of claim 2, wherein the atomic ratio of said at least one metal to the silicon in said molecular sieve in said contacting b) is from about 0.001 to about 3.0.

22. The method of claim 2, wherein the atomic ratio of said at least one metal to the silicon in said molecular sieve in said contacting b) is from about 0.01 to about 2.5.

23. The method of claim 2, wherein the atomic ratio of said at least one metal to the silicon in said molecular sieve in said contacting b) is from about 0.02 to about 2.0.

24. The method of claim 1, wherein the amount of metal in said organometallic treated molecular sieve is about 0.05% to about 20% by wt.

25. The method of claim 1, wherein the amount of metal in said organometallic treated molecular sieve is about 0.5% to about 10% by wt.

26. The method of claim 1, wherein the amount of metal in said organometallic treated molecular sieve is about 1% to about 8% by wt.

27. The method of claim 1, and further comprising calcining the molecular sieve prior to b).

28. The method of claim 27, wherein said calcining is carried out at temperature of about 300° C. to about 800° C. for a period of about 1 hour to about 24 hours.

29. The method of claim 27, wherein said calcining is carried out at temperature of about 450° C. to about 750° C. for a period of about 2 hours to about 12 hours.

30. The method of claim 27, wherein said calcining is carried out at temperature of about 550° C. to about 700° C. for a period of about 3 hours to about 10 hours.

31. The method of claim 27, wherein said calcining is carried out in the presence of oxygen.

32. The method of claim 1, wherein calcining the organometallic treated molecular sieve separated in c) is carried out at a temperature of at least 300° C.

33. The method of claim 32, wherein said calcining is carried out at temperature of about 300° C. to about 800° C. for a period of about 1 hour to about 24 hours.

34. The method of claim 32, wherein said calcining is carried out at temperature of about 450° C. to about 750° C. for a period of about 2 hours to about 12 hours.

35. The method of claim 32, wherein said calcining is carried out at temperature of about 550° C. to about 700° C. for a period of about 3 hours to about 10 hours.

36. The method of claim 32, wherein said calcining is carried out in the presence of oxygen.

37. The method of claim 1 and further comprising physically mixing the organometallic treated molecular sieve with an oxide of at least one metal selected from Group 2, Group 3 and Group 4 of the Periodic Table of Elements.

38. The method of claim 37, wherein said oxide is selected from oxides of zirconium, hafnium, magnesium, calcium, strontium, barium, yttrium, scandium, lanthanum, cerium, praseodymium, neodymium, samarium, thorium and mixtures thereof.

39. The method of claim 37, wherein the organometallic treated molecular sieve is physically mixed wit oxides of lanthanum and zirconium.

40. The method of claim 37, wherein said oxide has an uptake of carbon dioxide at 100° C. of at least 0.03 mg/m$^2$ of the metal oxide.

41. A catalyst composition comprising a calcined, organometallic treated molecular sieve prepared by the method of claim 1, physically admixed with one or more calcined active metal oxides selected from the group consisting of oxides of zirconium, hafnium, magnesium, calcium, strontium, barium, yttrium, scandium, lanthanum, cerium, praseodymium, neodymium, samarium, or thorium and mixtures thereof, after said molecular sieve has been treated with said organometallic compound.

42. The catalyst composition of claim 41, wherein said oxide is selected from oxides of zirconium, or lanthanum, and mixtures thereof.

43. The catalyst composition of claim 41, wherein said oxide has an uptake of carbon dioxide at 100° C. of at least 0.03 mg/m² of the metal oxide.

44. The catalyst composition of claim 41 and further comprising at least one of a binder and a matrix.

45. The catalyst composition of claim 44, wherein the binder and/or matrix is selected from alumina, aluminum chlorohydrol, clay, and mixtures thereof.

46. The catalyst composition of claim 41 wherein the molecular sieve is a silicoaluminophosphate.

47. The composition of claim 46, wherein the molecular sieve is SAPO-18, SAPO-34 or an intergrowth of SAPO-18 and SAPO-34 and the organometallic species is derived from dimethyl zinc or methylmagnesium bromide.

* * * * *